US011490832B2

(12) United States Patent
Murphy

(10) Patent No.: US 11,490,832 B2
(45) Date of Patent: *Nov. 8, 2022

(54) METHOD AND APPARATUS FOR DETERMINING ACETABULAR COMPONENT POSITIONING

(71) Applicant: Stephen B. Murphy, Winchester, MA (US)

(72) Inventor: Stephen B. Murphy, Winchester, MA (US)

( * ) Notice: Subject to any disclaimer, the term of this patent is extended or adjusted under 35 U.S.C. 154(b) by 439 days.

This patent is subject to a terminal disclaimer.

(21) Appl. No.: 16/556,844

(22) Filed: Aug. 30, 2019

(65) Prior Publication Data
US 2020/0008816 A1    Jan. 9, 2020

Related U.S. Application Data

(60) Continuation of application No. 15/298,988, filed on Oct. 20, 2016, now Pat. No. 10,398,455, which is a
(Continued)

(51) Int. Cl.
*A61B 5/107*  (2006.01)
*A61B 17/00*  (2006.01)
(Continued)

(52) U.S. Cl.
CPC ............ *A61B 5/107* (2013.01); *A61B 5/1071* (2013.01); *A61B 5/1072* (2013.01); *A61B 17/00* (2013.01);
(Continued)

(58) Field of Classification Search
CPC ..... A61B 5/107; A61B 5/1071; A61B 5/1072; A61B 5/1114; A61B 17/00; A61B 17/17;
(Continued)

(56) References Cited

U.S. PATENT DOCUMENTS

| 3,457,651 A | 7/1969 | Kaeck |
| 5,056,523 A | 10/1991 | Hotchkiss, Jr. et al. |

(Continued)

FOREIGN PATENT DOCUMENTS

| DE | 19521060 A1 | 12/1996 |
| DE | 102004010332 B3 | 10/2005 |

(Continued)

OTHER PUBLICATIONS

Archibald, H. A. P., et al., "The Transverse Acetabular Ligament: An Aid to Orientation of the Acetabular Component During Primary Total Hip Replacement: A Preliminary Study of 1000 Cases Investigating Postoperative Stability," British Editorial Society of Bone and Joint Surgery, Journal Bone Joint Surgery, vol. 88-B, No. 7, Jul. 2006, pp. 883-886.

(Continued)

*Primary Examiner* — Larry E Waggle, Jr.
(74) *Attorney, Agent, or Firm* — Cesari and McKenna, LLP

(57) ABSTRACT

An instrument for establishing orientation of a pelvic prosthesis comprises a hub, a first arm attached to and extending from the hub, and a second arm attached to and extending from the hub. The first and second arms define a nominal plane of the apparatus, and may extend from the hub at an angle relative to each other. Distances between the first and second legs and between the first and third legs are adjustable. The first, second, and third legs have tips, and the tips of the first, second, and third legs define a plane having a predefined geometric relationship to the nominal plane of the apparatus.

18 Claims, 5 Drawing Sheets

Related U.S. Application Data continuation of application No. 14/746,028, filed on Jun. 22, 2015, now Pat. No. 9,474,470, which is a continuation of application No. 13/537,654, filed on Jun. 29, 2012, now Pat. No. 9,101,378, which is a division of application No. 12/134,545, filed on Jun. 6, 2008, now Pat. No. 8,267,938.

(60) Provisional application No. 60/984,425, filed on Nov. 1, 2007.

(51) Int. Cl.
| | |
|---|---|
| A61B 17/17 | (2006.01) |
| A61B 17/56 | (2006.01) |
| B43L 7/10 | (2006.01) |
| G01B 3/56 | (2006.01) |
| G01B 5/24 | (2006.01) |
| A61K 45/06 | (2006.01) |
| A61K 31/409 | (2006.01) |
| A61K 31/44 | (2006.01) |
| A61K 31/555 | (2006.01) |
| F16C 11/10 | (2006.01) |
| A61F 2/46 | (2006.01) |
| A61B 90/11 | (2016.01) |
| A61B 90/00 | (2016.01) |
| A61B 34/10 | (2016.01) |
| A61B 5/11 | (2006.01) |

(52) U.S. Cl.
CPC .......... *A61B 17/17* (2013.01); *A61B 17/1746* (2013.01); *A61B 17/56* (2013.01); *A61B 34/10* (2016.02); *A61B 90/06* (2016.02); *A61B 90/11* (2016.02); *A61F 2/4609* (2013.01); *A61K 31/409* (2013.01); *A61K 31/44* (2013.01); *A61K 31/555* (2013.01); *A61K 45/06* (2013.01); *B43L 7/10* (2013.01); *F16C 11/10* (2013.01); *G01B 3/56* (2013.01); *G01B 3/563* (2013.01); *G01B 5/24* (2013.01); *A61B 5/1114* (2013.01); *A61B 2034/105* (2016.02); *A61B 2090/067* (2016.02); *A61B 2090/364* (2016.02); *F16C 11/103* (2013.01); *F16C 2316/10* (2013.01); *Y10T 403/32426* (2015.01)

(58) Field of Classification Search
CPC ..... A61B 17/1746; A61B 17/56; A61B 19/46; A61B 19/50; A61B 19/201; A61B 2017/5289; A61B 2090/067; A61F 2/4609; B43L 7/10; G01B 3/56; G01B 3/563; G01B 5/24

See application file for complete search history.

(56) References Cited

U.S. PATENT DOCUMENTS

| | | | |
|---|---|---|---|
| 5,086,401 A | 2/1992 | Glassman et al. | |
| 5,122,145 A | 6/1992 | Fishbane | |
| 5,127,920 A | 7/1992 | MacArthur | |
| 5,141,512 A * | 8/1992 | Farmer | A61B 17/1746 606/87 |
| 5,141,513 A | 8/1992 | Fortune et al. | |
| 5,320,625 A | 6/1994 | Bertin | |
| 5,327,907 A | 7/1994 | Fischer | |
| 5,376,093 A | 12/1994 | Newman | |
| 5,515,616 A | 5/1996 | Merkin | |
| 5,571,111 A | 11/1996 | Aboczky | |
| 5,697,939 A | 12/1997 | Kubota et al. | |
| 5,776,143 A | 7/1998 | Adams | |
| 5,824,007 A | 10/1998 | Faraz et al. | |
| 5,916,219 A | 6/1999 | Matsuno et al. | |
| 6,090,114 A | 7/2000 | Matsuno et al. | |
| 6,132,437 A | 10/2000 | Omurtag et al. | |
| 6,228,089 B1 | 5/2001 | Wahrburg | |
| 6,273,891 B1 | 8/2001 | Masini | |
| 6,290,196 B1 | 9/2001 | Mayenberger | |
| 6,314,312 B1 | 11/2001 | Wessels et al. | |
| 6,395,005 B1 | 5/2002 | Lovell | |
| 6,482,237 B2 | 11/2002 | Mosseri | |
| 6,634,883 B2 | 10/2003 | Ranalli | |
| 6,743,235 B2 | 6/2004 | Subba Rao | |
| 7,090,677 B2 | 8/2006 | Fallin et al. | |
| 7,182,766 B1 * | 2/2007 | Mogul | A61B 17/15 606/87 |
| 7,201,756 B2 | 4/2007 | Ross et al. | |
| 7,344,542 B2 | 3/2008 | Coliazo et al. | |
| 7,419,492 B2 | 9/2008 | Yoon et al. | |
| 7,651,501 B2 | 1/2010 | Penenberg et al. | |
| 7,780,672 B2 | 8/2010 | Metzger et al. | |
| 8,267,938 B2 | 9/2012 | Murphy | |
| 8,986,309 B1 | 3/2015 | Murphy | |
| 9,101,378 B2 | 8/2015 | Murphy | |
| 9,474,470 B2 | 10/2016 | Murphy | |
| 9,883,954 B1 | 2/2018 | Murphy | |
| 10,004,752 B2 | 6/2018 | Murphy | |
| 10,398,455 B2 * | 9/2019 | Murphy | A61K 31/44 |
| 2003/0153829 A1 | 8/2003 | Sarin et al. | |
| 2004/0092944 A1 | 5/2004 | Penenberg | |
| 2004/0152970 A1 | 8/2004 | Hunter | |
| 2004/0210233 A1 | 10/2004 | Yoon et al. | |
| 2004/0254586 A1 | 12/2004 | Sarin et al. | |
| 2004/0260312 A1 | 12/2004 | Magnusson et al. | |
| 2005/0076441 A1 | 4/2005 | Dominati et al. | |
| 2005/0107799 A1 | 5/2005 | Graf et al. | |
| 2005/0148843 A1 | 7/2005 | Roose | |
| 2005/0149050 A1 | 7/2005 | Stifter et al. | |
| 2005/0234332 A1 | 10/2005 | Murphy | |
| 2006/0025778 A1 | 2/2006 | Ferree | |
| 2006/0052795 A1 | 3/2006 | White | |
| 2006/0100504 A1 | 5/2006 | Jansen et al. | |
| 2006/0161167 A1 | 7/2006 | Myers et al. | |
| 2006/0184177 A1 | 8/2006 | Echeverri | |
| 2006/0225529 A1 | 10/2006 | Fischer et al. | |
| 2006/0241441 A1 | 10/2006 | Chinn | |
| 2008/0009697 A1 | 1/2008 | Haider | |
| 2008/0255584 A1 | 10/2008 | Beverland et al. | |
| 2008/0287954 A1 | 11/2008 | Kunz et al. | |
| 2009/0163922 A1 | 6/2009 | Meridew et al. | |
| 2009/0171370 A1 | 7/2009 | Yoon et al. | |
| 2009/0254093 A1 | 10/2009 | White et al. | |
| 2009/0306679 A1 | 12/2009 | Murphy | |
| 2011/0196433 A1 | 8/2011 | Kleiner | |
| 2012/0245647 A1 | 9/2012 | Kunz et al. | |
| 2013/0006255 A1 | 1/2013 | Murphy | |
| 2013/0018430 A1 | 1/2013 | Murphy | |
| 2015/0289891 A1 | 10/2015 | Murphy | |

FOREIGN PATENT DOCUMENTS

| | | | |
|---|---|---|---|
| JP | 2004-89653 A | 3/2004 | |
| JP | 2005-111257 A | 4/2005 | |
| JP | 2006-501972 A | 1/2006 | |
| JP | 2011-502626 A | 1/2011 | |
| SU | 441 933 | 9/1974 | |
| WO | WO 00/30557 | 6/2000 | |
| WO | WO 01/34017 | 5/2001 | |
| WO | WO 03/009768 | 2/2003 | |
| WO | WO/2004/021898 | 3/2004 | |
| WO | WO/2005/046451 | 5/2005 | |
| WO | WO-2005046451 A2 * | 5/2005 | ......... A61B 17/1739 |
| WO | WO/2006/109983 | 10/2006 | |
| WO | WO-2008/145287 A1 | 12/2008 | |

OTHER PUBLICATIONS

Chow, JC, et al., "Evaluation of Intraoperative Pelvic Positioning Using Software-based Computed Tomography/Radiography Matching," International Society for Computer Assisted Orthopedic Surgery, Jun. 2008, pp. 192-194.

(56) References Cited

OTHER PUBLICATIONS

English Description of Japanese Publication No. JP2004-089,653, retrieved on Aug. 27, 2014, pp. 1-30.

English Description of Japanese Publication No. JP 2005-111,257, retrieved on Aug. 27, 2014, pp. 1-26.

English Translation of Office Action, from Japanese Patent Office for Japanese Patent Application No. JP 2013-112536, dated Apr. 1, 2014, pp. 1-2.

European Search Report, European Application No. 13153277.2-1659 / 2626032, Applicant: Stephen B. Murphy, dated Mar. 20, 2014, pp. 1-6.

European Search Report, European Application No. 13153236.8-1659 / 2626031, Applicant: Stephen B. Murphy, dated Aug. 22, 2014, pp. 1-5.

Klingenstein, G., et al., "Pelvic Tilt Before and After Total Hip Arthroplasty," International Society for Computer Assisted Orthopedic Surgery, Jun. 2008, pp. 99-100.

Notification of Transmittal of the International Search Report and the Written Opinion of the International Searching Authority, or the Declaration, International Filing Date: Oct. 30, 2008, International Application No. PCT/US2008/012300, Applicant: Stephen B. Murphy, dated Mar. 5, 2009, pp. 1-8.

Chen, Bin, et al., "Personalized Image-Based Templates for Precise Acetabular Prosthesis Placement in Total Hip Arthroplasty: A Pilot Study," Journal of Zhejiang University—SCIENCE B (Biomedicine & Biotechnology), Sep. 11, 2010, pp. 673-680.

Murphy, Stephen, et al., "Evaluation of Intraoperative Pelvic Position During Hip Arthroplasty Using Computed Tomography/Radiography Matching," Oral Session 18, The $21^{st}$ Annual Congress of the International Society for Technology in Arthroplasty, Seoul Korea, Oct. 1-4, 2008, one page.

U.S. Appl. No. 15/887,604, filed Feb. 2, 2018 by Stephen B. Murphy, M.D. for an Acetabular Template Component and Method of Using Same During Hip Arthrosplasty, pp. 1-31.

U.S. Appl. No. 13/764,637, filed Feb. 11, 2013 by Stephen B. Murphy, M.D. for an Surgical System Using a Registration Device, pp. 1-39.

* cited by examiner

METHOD AND APPARATUS FOR DETERMINING ACETABULAR COMPONENT POSITIONING

CROSS-REFERENCE TO RELATED APPLICATIONS

This application is a continuation of application Ser. No. 15/298,988, filed Oct. 20, 2016, now U.S. Pat. No. 10,398,455, which is a continuation of application Ser. No. 14/746,028, filed Jun. 22, 2015, now U.S. Pat. No. 9,474,470, which is a continuation of application Ser. No. 13/537,654, filed Jun. 29, 2012, now U.S. Pat. No. 9,101,378, which is a divisional of application Ser. No. 12/134,545, filed Jun. 6, 2008, now U.S. Pat. No. 8,267,938, which claims the benefit of Provisional Application Ser. No. 60/984,425, filed Nov. 1, 2007, which applications are hereby incorporated by reference in their entireties.

FIELD OF THE INVENTION

The invention relates to determining acetabular component positioning, and provides a method and apparatus for rapidly and accurately determining such positioning.

BACKGROUND INFORMATION

Malpositioning of the acetabular component during hip arthroplasty can lead to dislocation, impingement, wear, and reoperation for all of these problems. Proper positioning of the acetabular component during hip arthroplasty requires that the surgeon know the position of the patient's pelvis during surgery so that the component can be inserted in proper position relative to the pelvis. Unfortunately, the position of the patient's pelvis varies widely during surgery and from patient to patient. As a result, large errors in component positioning occur if the surgeon assumes that the patient's pelvis is positioned squarely with the operating table, whether in the lateral or supine position. For example, one study showed that patients' pelvises were malpositioned through a range of 33 degrees around the medial-lateral axis, 47 degrees around the longitudinal axis, and 17 degrees around the anterior-posterior axis. (Chow J C, Eckman K, Jaramaz B, Murphy S, Evaluation of Intraoperative pelvic position during hip arthroplasty using computer tomography/radiography matching, International Society for Computer Assisted Orthopedic Surgery, 2008).

To reduce the likelihood of component malpositioning, the position of the pelvis can be tracked using computer-assisted surgical navigation techniques, but the majority of surgeons do not employ these techniques. More basic surgical technique involves qualitative assessment of the position of the acetabular component compared to the local surrounding bony and soft tissue anatomy that is visible through the incision. One such technique, for example, uses the transverse acetabular ligament as a qualitative marker of orientation of the native acetabulum. (Archbold H A, Mockford B, Molloy D, McConway J, Ogonda L, Beverland D, The Transverse acetabular ligament: an aid to orientation of the acetabular component during primary total hip replacement: a preliminary study of 1000 cases investigating post-operative stability, J Bone Joint Surg BR. 2006 July; 88(7): 883-6).

Unfortunately, such techniques have limited accuracy for several reasons. First, the transverse acetabular ligament is very close to the center of the acetabulum and thus geometrically small errors in interpretation of its position can lead to large angular errors in orientation of the acetabular component. Second, since the transverse acetabular ligament defines a line, which is a two dimensional geometric element: it does not provide true three dimensional guidance. Third, since most hips that are worn are also malformed, taking clues from the local malformed anatomy is a fundamentally flawed concept. Further, even if the local anatomy were not abnormal, as may be the case in patients with femoral head osteonecrosis, it is often the case that the native acetabulum is orientated in a much more vertical position than is appropriate for a prosthetic acetabulum. As a result, while the normally formed native acetabulum may provide clues as to where to position the prosthetic acetabulum, the prosthetic acetabulum should not be placed in the same orientation as the normal native acetabulum.

SUMMARY OF THE INVENTION

The local acetabular anatomy can be used to determine prosthetic acetabular component placement if the relationship of the local anatomy is known relative to overall orientation of the pelvis itself (such as the anterior pelvic plane) and the spino-pelvic composite. Conversely, if that relationship is not known, the local acetabular anatomy may not reliably be used in determining the position of the prosthetic acetabular component. I have concluded that the anatomy of the ipsilateral hemipelvis, not the local acetabular anatomy, should be used to guide the positioning of a prosthetic acetabular component.

Using the ipsilateral hemipelvic anatomy to guide the orientation of the prosthetic acetabular component has several advantages over using local anatomy. First, it is the acetabulum itself, not the hemipelvis, that is typically altered by the arthritic process. Second, parts of the hemipelvis are relatively distant from the center of the acetabulum and so small errors in positioning based on the more distant hemipelvic bone leads to very small errors in orientation of the acetabular component. Third, while there is wide variation in local anatomy due to the arthritic process or due to malformation, there are relatively smaller variations in hemipelvic anatomy, and these variations can be easily studied by CT imaging or plain radiographs, or can be predicted statistically.

I have found that there are three points that may be used to dock an instrument to the ipsilateral hemipelvis to help solve the problem of acetabular component positioning during hip arthroplasty. These three points define an ipsilateral hemipelvic plane. While these may be any three points on the ipsilateral hemipelvis that are located some distance apart from one another, an ideal combination of points includes a first point, $P_1$, in the region of the ischium as it joins the posterior wall of the acetabulum; this point is referred to herein as the Anchor Point. The ease of identification of this point through most incisions for hip surgery, its resistance to alteration due to the arthritic process, its position (out of the way of most surgical maneuvers performed during reconstructive surgery), and its reliable consistency of formation, even in hips that have been severely malformed since birth, make this location an ideal location for an anchor.

A second point, $P_2$, to be used in forming the Ipsilateral Hemipelvic Plane is located on the lateral surface of the iliac wing, immediately adjacent to the anterior superior iliac spine. This location is a commonly used location in general, but is unique in its use in the current application. The anterior superior iliac spine is a reference point that is frequently used for many things in orthopedics. In clinical examination, it is frequently used as the proximal landmark to measure leg length. In combination with the contralateral anterior superior iliac spine, the position of the pelvis around an antero-posterior axis can be judged so that internal and external rotation or adduction and abduction of the hip joint can be clinically measured. In surgery performed in the supine position, abduction of an artificial cup can be roughly estimated relative to a horizontal line drawn between the two anterior superior iliac spines. In image-free computer assisted surgery, the anterior pelvic plane can be determined by digitizing the two anterior superior iliac spines and the pubic symphysis. In image-based computer assisted surgery, the location of the anterior superior iliac spine can be used as one of many points to perform registration to a CT dataset acquired pre-operatively.

Like other uses of the anterior superior iliac spine, the preferred location of $P_2$ on the surface of the lateral ilium in very close proximity to the anterior iliac spine takes advantage of the fact that this area is readily palpable by the surgeon and can be more precisely palpated by a sharp instrument that touches the bone. However, unlike other common uses of the region of the anterior superior iliac spine, in the current invention, this point is used as one of three points to define an ipsilateral hemipelvic plane. The distance between $P_1$ and $P_2$ can be calculated from CT studies, predicted from X-rays, or other imaging procedures; or even directly measured by the surgeon at the time of surgery. It can be fixed by the surgeon when he/she selects this desired point on the ilium; or it can be selected based on available or future statistical studies of pelvic anatomy, considering such factors as age, weight, sex, race, health and other parameters.

It will be noted that of the three degrees of freedom required to define the location of $P_2$ in space, one of them is inherently fixed by the bone surface itself; one is fixed by selecting the distance $d_{1-2}$; and one is fixed by the surgeon when he/she places the point at a specific location on the surface and at a given distance from $P_1$. The fact that the surgeon is defining only one of these three parameters necessary to identify $P_2$ in space makes this point a very reliable one to identify, and very resistant to variation or significant error.

The third point, $P_3$, that defines the ipsilateral hemipelvic plane may be located anywhere on the ipsilateral hemipelvis. For both mathematical stability and for the physical stability of an instrument designed to dock on these points, it is best that $P_3$ be as far distant from Points 1 and 2 as is reasonably practical within the limits of the hemipelvic surface; in a region where no vital structures will be encountered; on a region of the bone that is relatively dense, so that an instrument docked on this point will typically not inadvertently penetrate through the bone; and in a region where the bone surface is at least locally relatively flat so that an instrument docked to this point on the surface will not slip.

These three points, taken together, give very reliable information regarding the position of the ipsilateral hemipelvis and thus the position of the overall pelvis, and a mechanical instrument docked to these three locations therefore provides a guide for the proper relative orientation of the acetabular component itself during surgery.

Although the location of $P_3$ may be established in a variety of ways, I have found that it may be established very simply by locating it at a prescribed ratio "r" of the distance $d_{1-2}$ between P1 and P2 such that the distance $d_{1-3}$ between $P_1$ and $P_3$ is given by $\_d_{1-3}=r \cdot d_{1-2}$, where the operator "·" denotes multiplication. Similarly, the distance $d_{2-3}$ between $P_2$ and $P_3$ is given by $d_{2-3}=r' \cdot d_{1-2}$, where r' is likewise a prescribed ratio of the distance $d_{1-2}$ between $P_1$ and $P_2$. r and r' may be the same or a different ratio.

I have found that ratios r, r' of from approximately seventy percent to approximately one hundred percent of the length $d_{12}$ nearly always positions $P_3$ on a flat surface of the ilium, on generally firm bone, proximal and anterior to the sciatic notch. Within this range, I have found a ratio of approximately ninety percent to be most often satisfactory, with both r and r' approximately the same, i.e., r=r'=0.90. Although any ratio or combination of ratios between the $P_3$ and Points 1 and 2 may be sufficient, a ratio of approximately this magnitude reliably places $P_3$ away from vital structures that might be harmed by a different positioning. Further, providing a sufficiently distant spacing of the points in this manner provides an intrinsic stability to an instrument that is docked to them. Additionally, of the three degrees of freedom of $P_3$, one is prescribed by the distance from $P_1$, the second is prescribed by the distance from $P_2$, and the third is prescribed by the surface of the bone itself. Therefore, the location of $P_3$ is entirely determined by the surgical instrument and the bone surface, and is not subject to variable interpretation by the surgeon.

As discussed above, the three Points define an ipsilateral pelvic plane. The orientation of this plane with respect to a standard reference plane such as the anterior pelvic plane may readily be determined from CT or other method of 3D imaging, from X-ray imaging, by average, by statistics, or by other known techniques. Thus, the orientation of a prosthetic component defined in relation to this ipsilateral hemipelvic plane may readily be converted to an orientation relative to another plane such as the anterior pelvic plane, a standard reference for pelvic surgery.

For example, preoperatively, one may create a three-dimensional model of the patient's pelvis and hips based on medical imaging such as CT or MR and define the anterior pelvic plane (APP) from this model in the usual manner (typically, by marking the pubic symphysis or pubic tubercles and right and left anterior superior iliac spines). This is the reference plane commonly used by surgeons because the landmarks can readily be palpated so as to correlate the CT image with the patient anatomy. Next, an ipsilateral plane is defined on the 3D model in accordance with the invention, i.e., a first point in the region of the posterior inferior acetabulum, a second point adjacent to the anterior superior iliac spine, and a third point, preferably on the ilium, and spaced from the other two. As mentioned above, I have found that the third point is advantageously spaced from the first and second points at a distance of about from 0.7 to 1.0 times the distance between the first and second points, preferably at around 0.9 or 0.8. Although the spacing between the first and third points and between the second and third points need not necessarily be the same, I have found that an approximately equal spacing usually works well.

To assist the surgeon in defining the desired orientation of the prosthetic acetabulum relative to the ipsilateral pelvic plane, I have devised an instrument that accurately and rapidly facilitates fixing the location of $P_2$ and $P_3$, once the anchor point, P1, is selected by the surgeon. The instrument is essentially a tripod, i.e., it has three legs, one for each Point that is to define the ipsilateral pelvic plane. In use, a first leg is positioned by the surgeon at the anchor point on the pelvis. The second leg is positioned by the surgeon at the selected point, $P_2$, on the pelvis. The third leg is adjusted to extend a selected distance or distances from both $P_1$ and $P_2$ on the pelvis and thereby establishes the location of P3.

An acetabular direction guide is then placed on the tripod. The guide is adjustable to any desired orientation relative to the tips of the tripod legs (which coincides with the three Points on the pelvis when the instrument is rested on the pelvis). The orientation of the acetabular direction guide is selected by the surgeon as providing the desired orientation for insertion of a prosthetic component. The guide itself may be used to direct the orientation of the acetabular component, or the guide may be used to direct the insertion of a pin into the pelvis which will guide the ultimate insertion of the prosthetic component at the selected orientation.

The tripod may take a number of forms. For example, it may take the form of a camera tripod, in which three legs emanate from a central socket which enables adjusting the angles between each pair of legs (and thus the distance between their tips). Preferably, however, it takes the form of a generally planar frame having two arms extending generally from a common hub and oriented at an angle to each other. Legs located on the hub and on each arm, respectively, extend outwardly from the planar frame. Advantageously the legs extend perpendicular to the plane of the frame and are preferably of equal length. The tips of the legs contact the pelvis, and thereby establish the three points that define the pelvic plane.

In one implementation of the invention described herein, the tripod takes the form of a pair of extensible arms emanating from a central hub around which the arms pivot, much like a draftsman's compass. The lengths of the arms are adjustable by the surgeon, as is the angular opening between them. The three legs extend perpendicularly from the plane defined by the arms, with one leg extending from the central hub and the two other legs extending from the ends of the arms.

In another implementation of the invention, the tripod takes the form of a pair of extensible arms emanating from the central hub at a fixed angle, but is essentially the same as the implementation described immediately above.

In still another implementation, the leg that is positioned at $P_1$ is a hollow leg that slides over a guide pin that is drilled or screwed into the bone at P1. In use, the surgeon first fixes the guide pin into the bone at the desired location, then slides one of the legs of the tripod instrument over the guide pin. This anchors the instrument. The legs that land at $P_2$ and $P_3$ are preferably pointed to pierce the skin and stay firmly on the bone surfaces at $P_2$ and $P_3$ without slipping.

BRIEF DESCRIPTION OF THE DRAWINGS

The invention description below refers to the accompanying drawings, of which.

DETAILED DESCRIPTION OF ILLUSTRATIVE EMBODIMENTS OF THE INVENTION

Figure 1:
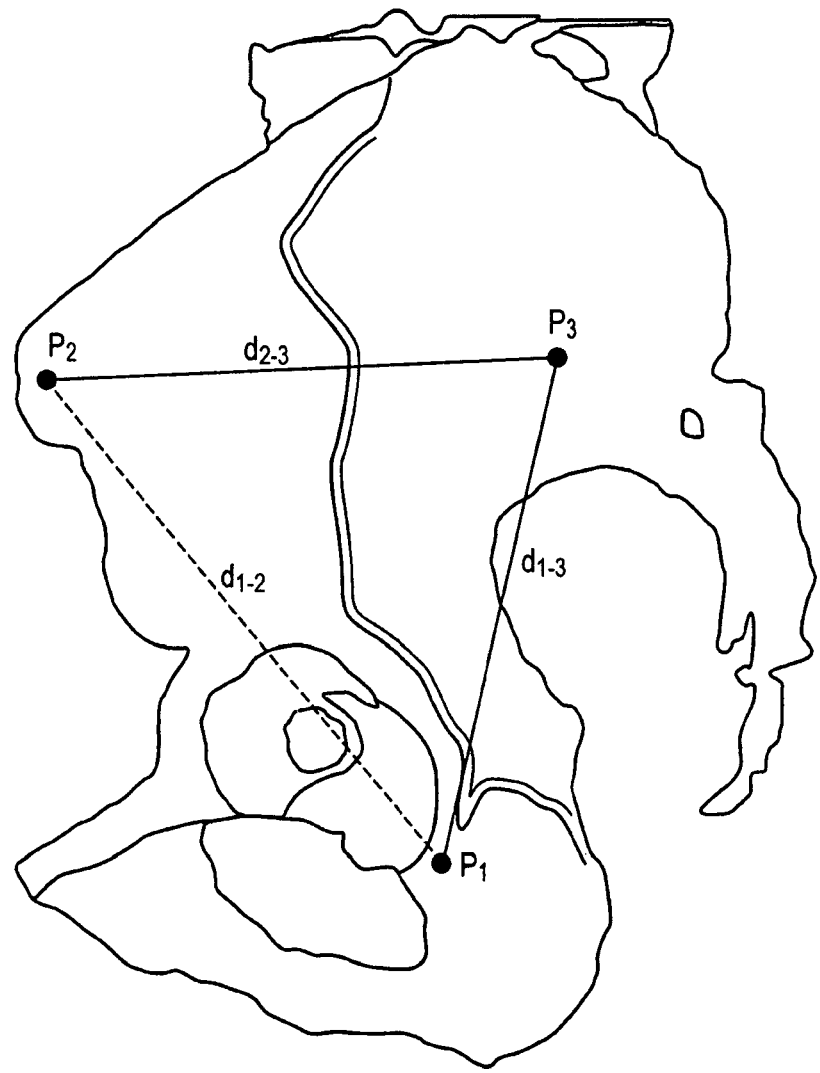
FIG. 1 is a schematized view of a left pelvis showing three points for defining an ipsilateral hemipelvic plane in accordance with the invention.

FIG. 1 is schematized view of a right pelvis showing the three points in question. Distance $d_{1-2}$ is the distance between the first point, $P_1$, (a point located on the ischium as it joins the posterior wall of the acetabulum) and the second point, $P_2$, a point located on the lateral surface of the iliac wing, immediately adjacent to the anterior superior iliac spine. Distance $d_{1-3}$ is the distance between the first point, $P_1$, and the third point, $P_3$ (on the ilium); and distance $d_{2-3}$ is the distance between the second point, $P_2$ and third point $P_3$. The distance $d_{1-2}$ is the baseline; the distances $d_{1-3}$ and $d_{2-3}$ are set at a distance of from 70% to 100% of the baseline distance, preferably about 80-90%. In FIG. 1 they are shown as being approximately 80-85% of the baseline distance. In FIG. 1, distances $d_{1-3}$ and $d_{1-3}$ are shown as approximately of equal length, although, as noted above, they need not necessarily be so. These three points, $P_1$, $P_2$, and $P_3$ define an ipsilateral plane.

The surgeon defines the desired orientation of the prosthetic acetabular components and the alignment indicator with respect to this ipsilateral pelvic plane. This may be done directly with respect to the ipsilateral pelvic plane so defined, or it may be done with reference to the anterior pelvic plane as established, for example, from a 3D computer model of the patient's pelvis based on CT, MR, or other imaging. While patient specific individual 3D models may be the most accurate method, other methods of determining the desired orientation of the alignment indicator and the ipsilateral pelvic plane based on statistical averages of pelvic structures and sizes of patients of similar size, sex, weight, age and/or other known characteristics may be used.

Figure 2:
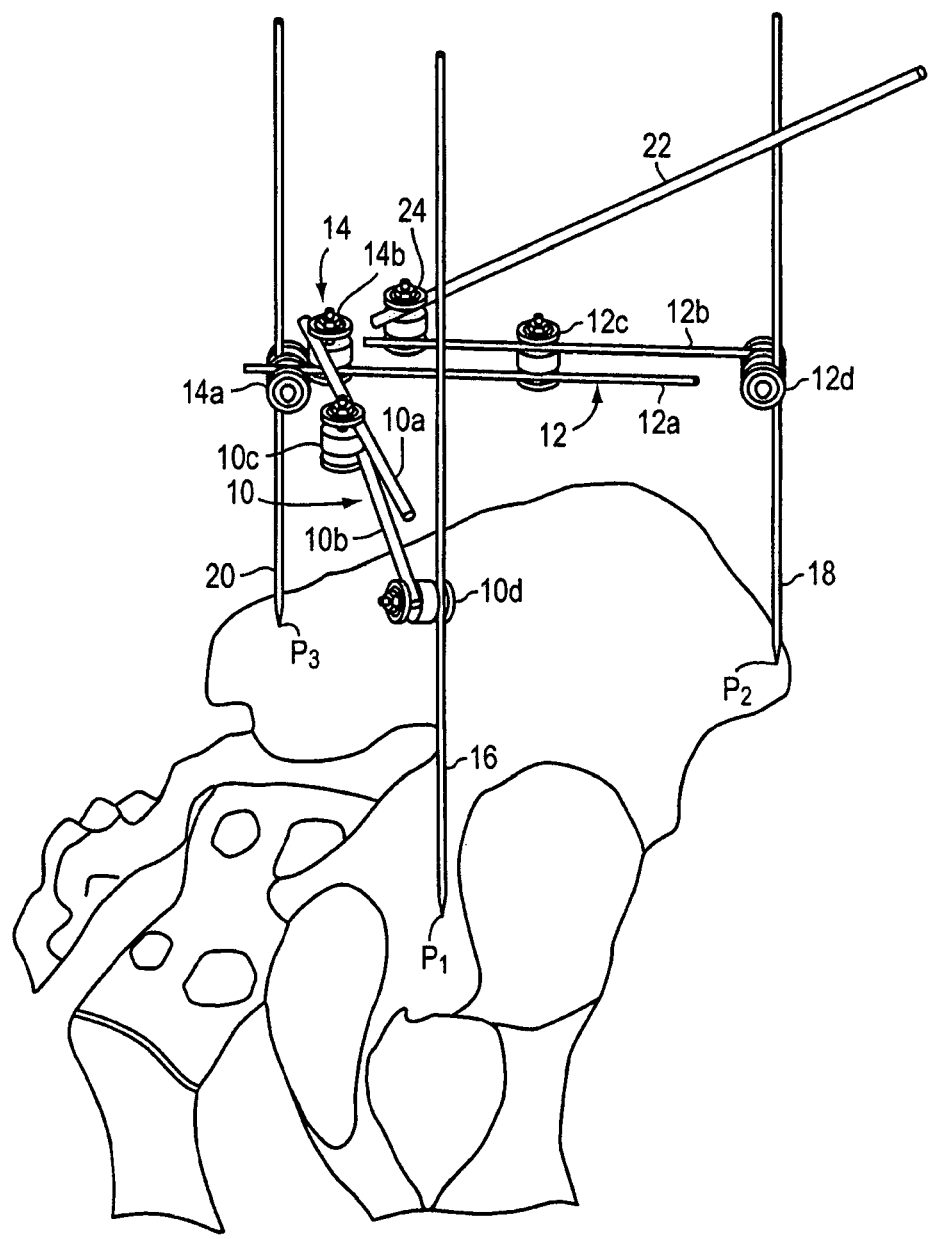
FIG. 2 is a view in perspective of a prototype instrument used to test the concept of the invention.

FIG. 2 is a view in perspective of a prototype instrument used to test the concept of the present invention. The prototype was formed from readily-available components in order to quickly test the concept. The instrument has first and second arms in the form of metal rods 10, 12, respectively, emanating from a hub 14 comprising first and second adjustable clamps 14a and 14b to hold the arms 10, 12, respectively, in a desired positioned when tightened. Arm 10 was formed from rods 10a and 10b secured together by an adjustable clamp 10c to enable extension of rod 10b with respect to rod 10a to a desired position. Similarly, arm 12 was formed from rods 12a and 12b secured together by an adjustable clamp 12c to enable extension of rod 12b with respect to rod 12a to a desired position.

At the outer extremity of arms 10b and 12b are legs in the form of rods 16 and 18, respectively, held in adjustable clamps 10d and 12d, respectively. Similarly, a leg in the form of a rod 20 extends from clamp 14a. In the prototype, the clamps were formed from readily available washers and nuts which can be loosened and tightened to hold a component in a desired position. The legs 16-20 were standard trochars having a pointed tip to enable extension through the skin of a patient and secure lodgment on the pelvic bone. The legs extended downwardly the same distance from the arms 10 and 12 and the hub 14 and thus the arms were essentially in a plane parallel to the plane defined by the tips of the legs.

The legs are shown positioned on a model of the pelvic anatomy for performance of a surgical procedure on the right acetabulum. The first leg, 16, rests on a point, P1, the anchor point, located on the ischium as it joins the posterior wall of the acetabulum. The second leg, 18, rests on a point, P2, located on the lateral surface of the iliac wing, immediately adjacent to the anterior superior iliac spine; the third leg, 20, rests on a point, P3, on the ilium; the location of this point is determined by the length of the arms 10 and 12 as set by the surgeon, as well as the relative angular orientation of these arms and the surface of the bone.

A direction guide 22 is adjustably secured to the frame. This guide will define the orientation for insertion of a prosthesis or the performance of other surgical procedures. The orientation of the guide with respect to the reference points $P_1$, $P_2$, and $P_3$ is established by the surgeon in pre-operative or intra-operative planning. When placed on a patient in the manner described above, the instrument defines an ipsilateral pelvic plane with respect to which the orientation of the guide 22 may readily be established by imaging, by direct measurement, or by other known means. From CT or other imaging studies, the orientation of this plane with respect to the commonly used anterior pelvic plane may be determined, and thus the orientation of the guide with respect to the anterior pelvic plane may be established if desired. During subsequent surgery, when the instrument is positioned on the patient in accordance with the reference points, the guide provides the surgeon with a reference axis for insertion of a prosthesis such as an acetabulum at a desired orientation. In the prototype, the guide was secured to one of the arms (e.g., arm 12) by means of an adjustable clamp 24. Although the guide is shown in FIG. 2 as a simple solid rod, it may advantageously be a hollow tube through which a pointed rod may be inserted into the patient. The rod is screwed into the bone and the instrument then removed, leaving the rod as the guide for acetabular component insertion or other procedure. Alternatively, a hollow tube may be mounted parallel to the guide and a pin inserted through this tube into the patient's bone to set the desired orientation for insertion of a component or for other surgical procedure.

In use, the surgeon places the patient in an appropriate position for the procedure to be performed. For example, in replacing the acetabulum of the right pelvis of a patient, the patient may be placed on his or her left side and a surgical field of sufficient size is created in order to expose the right acetabulum. The surgeon selects the point P1, preferably in the region of the ischium as it joins the posterior wall of the acetabulum. This is the Anchor Point, and is generally exposed in the surgical field during the operation, so that it is readily located. Leg 16 is positioned on this point. The surgeon next selects a point, P2, on the lateral surface of the iliac wing, preferably immediately adjacent to the anterior superior iliac spine. This region is usually readily located by palpation, and need not be within the exposed incision, but rather simply within the sterile surgical field. The surgeon then adjusts the length of arm 10 (and, if necessary, arm 12) to position leg 18 on P2, while ensuring that leg 20 lands on the hemipelvis, and preferably on a relatively flat area so that the leg will not slip. This defines point $P_3$.

Placing the first and second legs on the patient as discussed above, and fixing the distances $d_{1-3}$ and $d_{2-3}$ between the legs in the manner discussed above, fixes the point at which the third leg of the instrument will land on the patient. For acetabular component placement, this point will preferably be on the ilium, generally above the sciatic notch. The area in which it lands is a relatively strong portion of the anatomy, and thus is amenable to receiving the third leg to provide a stable reference plane on the patient. However, it is devoid of significant landmarks, and thus without the aid of the present instrument would not serve as an area which would help to establish a reference for component placement.

As noted previously, a simple but effective rule for adjusting the lengths of the arms 10, 12 is to set the distance $d_{1-3}$ between P1 and P3, as well as the distance $d_{2-3}$ between P2 and P3, at some ratio of the distance $d_{1-2}$ (the baseline distance) between P1 and P2. A ratio of from about 70% to 100% appears to work satisfactorily, but I have found that a ratio of about 80-90% works well in most cases.

Figure 3:
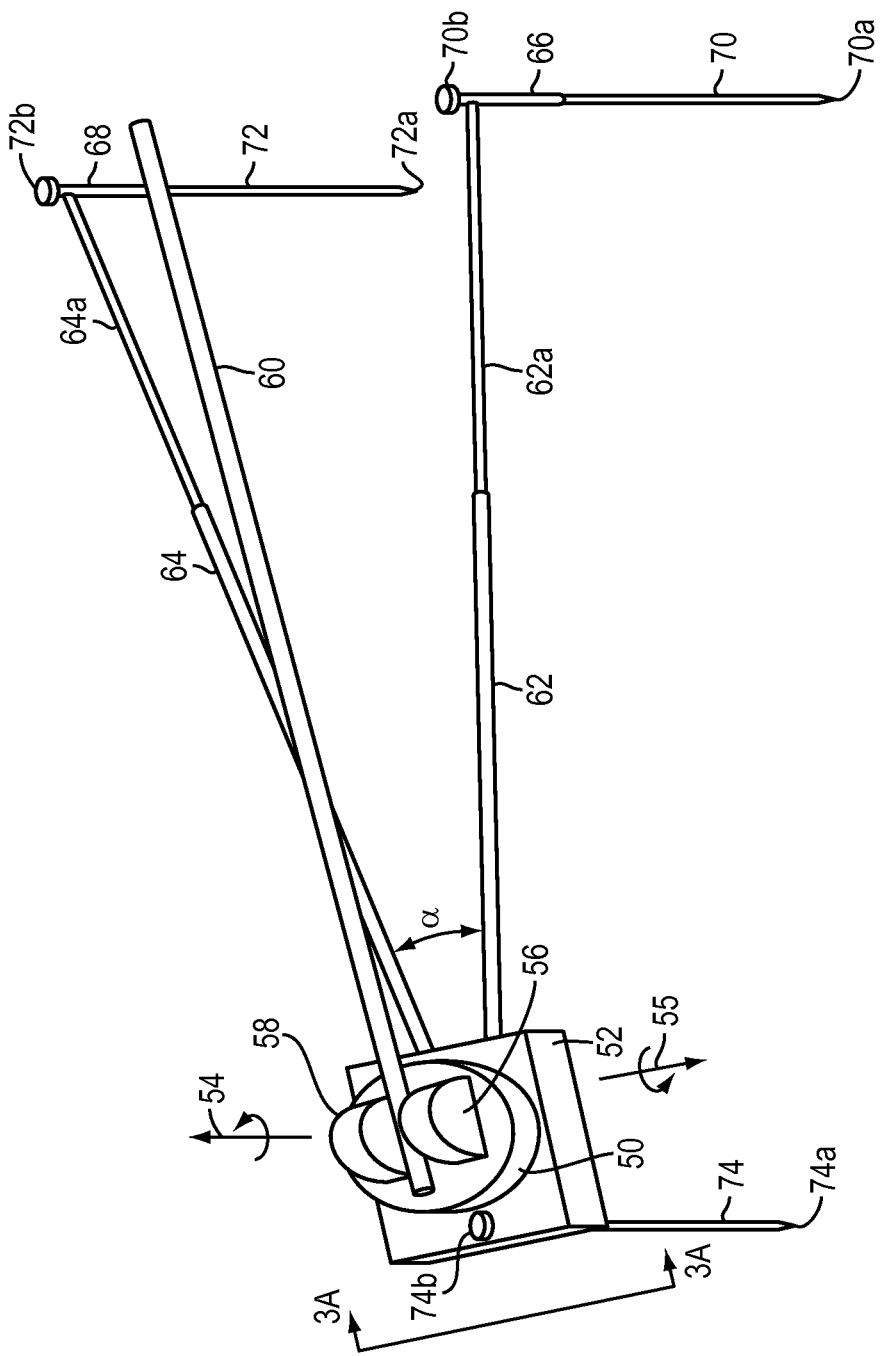
FIG. 3 is a view in perspective of one embodiment of an instrument suitable for use in establishing the reference planes and orientations in accordance with the invention.
Figure 3A:
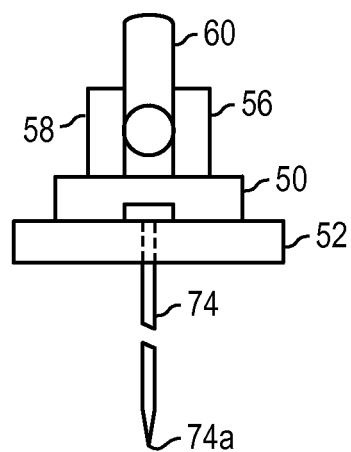
FIG. 3A is a partial view of the instrument of FIG. 3 form the direction 3A-#A in FIG. 3.

FIG. 3 is a view in perspective of another embodiment of an instrument in accordance with the invention that is more suited for replication and widespread use. A turret 50 is pivotally mounted on a base 52 for rotation about a vertical axis 54. (In this connection, it will be helpful to view also FIG. 3A which is a partial view of the instrument from the direction 3A-3A in FIG. 3). Wings 56, 58 on the turret mount a guide 60 for rotation in a vertical plane about a horizontal axis 55 that is transverse to axis 54. First and second extensible arms 62, 64 are mounted in base 52 for rotation with respect to the base and thus to each other. This enables the surgeon to adjust the angle α between the arms as desired. Of course, this may also be accomplished with one fixed arm and one rotatable arm. (It will also be understood that both arms may be fixed at a set angle α).

Figure 3B:
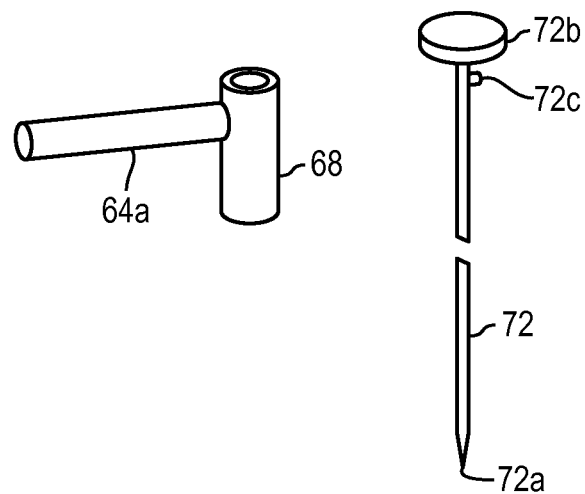
FIG. 3B is an illustrative sketch showing the fitting of a leg to a conduit.

Extensions 62a, 64a, extend from arms 62, 64, respectively. The extensions 62a, 64a may telescope from their respective arms as shown in FIG. 3, for example, in a manner similar to that of a camera tripod. Alternatively, they may be mounted for sliding overlap with these arms or may use other known forms of extension. Mounted at the ends of extensions 62a, 64a are hollow guides 66, 68, respectively. Legs 70, 72, have sharpened tips 70a, 72a, respectively, and heads 70b, 72b, respectively. The legs preferably also have a short boss 72c (see FIG. 3B) for mating with a corresponding groove on the interior surface of conduits 66, 68. The legs extend downwardly from the arms and the hub to the same extent, and thus the arms are essentially in a plane parallel to the ipsilateral plane formed by the tips of the legs.

In use, the surgeon grasps the heads 70b, 72b of the legs 70, 72 and inserts them into the conduits 66, 68 so that the bosses 72c align with the corresponding grooves in the respective conduit. He or she then rotates the heads to thereby removably lock the legs into the guides. In similar fashion, a leg 74 having a sharpened tip 74a and a head 74b is removably insertable into, and lockable within, the base 52. This construction facilitates cleaning of the instrument by enabling the rapid disassembly and reassembly of the legs. Of course, the legs could also be permanently fixed to the respective arms.

The tips 70a, 72a, and 74a of the legs 70, 72, 74, respectively, define a plane, the ipsilateral plane. Axis 54 is perpendicular to this plane, while axis 55 is parallel to it. Thus, the orientation of guide 60 relative to the ipsilateral plane is defined by the orientation of the guide relative to axis 55 (which defines the azimuthal orientation or angle of the pointer) and axis 54 (which defines the elevational orientation or angle of the pointer). To facilitate setting or determining these angles, scales (not shown) may be attached to, or marked on, the turret 50 and the base 52.

The instrument of FIG. 3 is used in the same manner as that of FIG. 2, i.e., for operation on the right hip, the tip of leg 70 is located on the selected point P1, the tip of leg 72 is located on selected point P2, and the lengths of these legs (as well as the angle α if appropriate) is adjusted to ensure that the tip of leg 74 lands on the hemipelvis, preferably in a relatively flat region, to thereby fix point $P_3$. This orientation of the instrument thereby recreates the ipsilateral plane defined in the preoperative studies. When the guide 60 is then set to the angles determined as desirable in the preoperative studies, it is oriented with respect to the patient in the desired manner. It may then be used to guide the component insertion tools along the appropriate direction. To do this, the surgeon may simply visually align the tool with the guide during the insertion. Preferably, however, the guide 60 is hollow and an elongated pin is extended down the guide while it is in the desired position on the patient, and the pin is then anchored into the patient. The instrument may then be removed, the pin preserving the desired orientation for placement of the prosthesis.

The important parameters of the instrument can be easily adjusted so that the instrument can effectively be customized to each patient in a very short period of time, taking just a minute or two, and can be done while the instrument is sterile on the operating table. Important adjustments are the lengths of arms 62 and 64, the angle between these arms, and the orientation of the alignment indicator. While the angle (alpha) between arm 1 and arm 2 can be adjustable, the preferred angle can be fixed at approximately 67.5 degrees, which is the angle defined if the distances between P1 and P3 and between P2 and P3 are both 0.9 times the distance between P1 and P2. Similarly, while the length of arms 60 and 62 need not be the same, the preferred embodiment of the instrument is such that the arms are of approximately the same length relative to each other, although the length of arm 1 and arm 2 varies from one individual to the next.

The patient-specific adjustable variables for each operation then are the lengths of the arms and the orientation of the alignment indicator or guide relative to the plane of the instrument body. The lengths of the arms can be determined before surgery or even during surgery using a number of methods, each with a differing degree of precision. The most precise method of determining the desired lengths of the arms is by three dimensional imaging of the individual patient, typically by CT or MR imaging. In this way, points P1 and P2 can be determined by the surgeon on the computer model and the location of P3 can be automatically calculated as the unique point lying on the bone surface at a specified distance from P1 and P2. Less precise, but potentially suitable methods of determining the lengths of the arms include:

1. An overall average of all patients;
2. An overall average of all patients of the same sex, height, weight, diagnosis;
3. As statistically predicted from measurements from magnification corrected plain radiographs of the patient to be treated and matching those radiographs statistically with radiographs and three-dimensional reconstructions of similar patients who have had CT, MR, or other methods of deriving three-dimensional models. This method can be referred to as 2D to 3D statistical modeling; or
4. Directly measuring the distance between P1 and P2 at surgery, which can even be performed using the instrument itself.

Next, the orientation of the alignment indicator relative to the plane of the instrument body must be decided. This determination is based on two or more factors. The first is the relative orientation of the hemipelvic plane (P1, P2, P3) relative to the overall pelvis and/or the anterior pelvic plane. The second is the surgeon's desired cup position relative to the overall pelvis and/or the anterior pelvic plane in the case of acetabular cup replacement surgery. Finally, an additional variable might include an adjustment for anticipated orientation of the overall pelvis for various activities and positions after surgery. This third variable is mentioned because there are variations in the way different patients' pelvises are orientated, some with more pelvic tilt and some with less pelvic tilt. (Klingenstein G, Eckman K, Jaramaz B, Murphy S. Pelvic Tilt Before and After Total Hip Arthroplasty, International Society for Computer Assisted Orthopedic Surgery, 2008). This is particularly true of patients with a fused lumbosacral spine. If the individual postoperative patient pelvic orientation can be predicted preoperatively, then this factor can be incorporated into the planning of the desired orientation of the alignment indicator.

As with determination of the lengths of the arms, orientation of the alignment indicator can be determined by the above combined with knowledge of the anatomy of the individual patient's pelvis, aided by determination of one or more of the factors discussed above. Using these methods of adjusting the instrument body, adjusting the alignment indicator, and applying the instrument in surgery, the desired orientation of an acetabular component can be rapidly and reliable determined during surgery. Further, the method avoids the unreliable influences of local anatomy that is frequently deformed and further distorted by the arthritic process.

Figure 4:
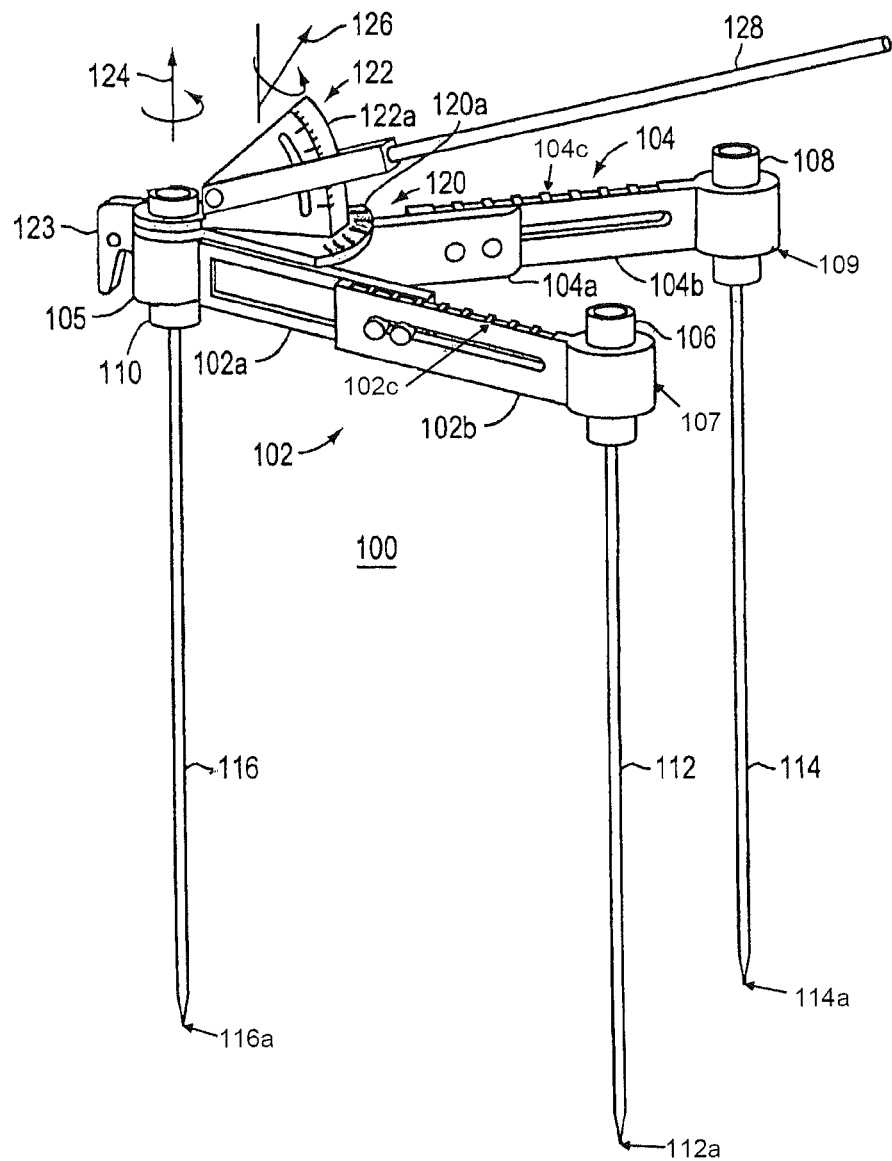
FIG. 4 is a view in perspective of yet another embodiment of an instrument suitable for use in establishing the reference planes and orientations in accordance with the invention.

FIG. 4 shows yet another embodiment of the invention in which the extensible arms are formed by slidable beams and in which the conduits holdings the legs are themselves removable for ease in cleaning. In particular, the instrument has first and second arms 102 and 104 formed from first and second arm segments 102a and 104a, respectively, fixed to and extending from a hub in the shape of a cylindrical conduit 105 having a central bore extending therethrough. Markers 102c, 104c on arm segments 102b, 104b, respectively, indicate the amount of extension of the arm segments, and thus the length of the arms. In the configuration shown, the arm segments 102a, 104a are positioned at a fixed angle to each other, advantageously on the order of 67.5 degrees.

A mating rod segment 110 having a leg 116 extending therefrom is snugly but removably press-fitted into the conduit 105 to form one leg of the tripod 100. Similarly, rod segments 106 and 108, having legs 112, 114, respectively, extending therefrom are snugly but removably press-fit into hollow-bored conduits 107, 109, respectively, formed on the ends of arms 102b, 104b, respectively. Removal of the legs facilitates sterilization of the instrument before each use, and also makes the instrument more compact for storage.

A first plate 120 is fixed to the hub 105; the plate has a scale 120a thereon. A second plate 122 is pivotally mounted on the hub 105 for rotation in the horizontal plane about a vertical axis 124 with respect to the first plate 120. A releasable lock 123 fixes the angular orientation of the plate at the orientation set by the surgeon. A guide 128 is pivotally mounted on the second plate for rotation in the vertical plane about a horizontal axis 126. Plate 120 has a scale 120a for indicating the angular orientation of the plate 122 with respect to it (the azimuthal angle). Similarly, plate 122 has a scale 122a for indicating the angular orientation of the guide 128 with respect to the plate (the elevation angle). As was previously the case, the tips 112a, 114a, and 116a of legs 112, 114, 116, respectively, define a plane (the ipsilateral hemipelvic plane) and the arms 102 and 104 are parallel to this plane. Thus, the orientation of the guide can be referred to this plane and thus also to the anterior pelvic plane if desired.

In this embodiment, the conduits 112, 114, 116 are detachable from the arms 102 and 104 and the hub 105, respectively. Advantageously, they may simply form a force-fit, although other means of connation may be used. This facilitates sterilizing the instrument for repeated use, while enabling its ready reassembly in the operating room. It also enables the instrument to be stored in a more compact package.

In still a further variation of the instrument of FIG. 4, one of the legs, e.g., the leg 112, rather than being removable, may in fact comprise a hollow conduit of the same length as the legs 114 and 116. With this configuration, the surgeon may first select the anchor point $P_1$, insert a pointed rod (trochar) into the anchor point, slide the hub 106 onto the rod, and then position the legs accordingly as described above, while being sure that the instrument frame will not slide from the hip during positioning.

A further variation in the use of the instrument involves its combination with computer-assisted surgical navigation using optical, electromagnetic, or other means of tracking. In any of these processes, a coordinate system for the pelvis must be defined, where this coordinate system may be the anterior pelvic plane or another plane. Since the mathematical relationship between the ipsilateral hemipelvic plane, as defined by the mechanical instrument, and any other plane, such as the anterior pelvic plane, can be determined preoperatively, placement of the instrument onto the ipsilateral hemipelvis and then measurement of its location using a navigation system can be used to rapidly determine the orientation of the pelvis. The mechanical instrument can then be removed and surgical navigation can proceed as usual thereafter.

Similarly, surgical navigation can be facilitated by rapidly determining the overall orientation of the pelvis using the same method as above, but with a virtual mechanical instrument. In this way, P1 is determined by the surgeon using a digitizer (optical, electromagnetic, or other). Next, the surgeon defines P2 using the digitizer. The virtual instrument defines the distance P1-P2 and so P2 must lie on a sphere whose radius is P1-P2 and must also lie on the bone surface. As such, two of three degrees of freedom for determining the point P2 are predetermined and only one of the three degrees of freedom for determining the point P2 is subject to surgeon choice. This greatly improves the accuracy of determining this point. Finally, the surgeon defines P3 using a digitizer. Using the virtual instrument, the location of point P3 must lie on the bone surface, must be a specified distance from point P1, and must be a specified distance from point P2. Thus, the virtual mechanical instrument defines all the three degrees of freedom that determine the location of the point P3 and its location is not subject to surgeon choice. Further, this very specific point can be determined on a flat, indistinct surface where there are no palpable landmarks.

What is claimed is:

1. An apparatus comprising:
   a hub;
   a first arm attached to and extending from the hub;
   a second arm attached to and extending from the hub, where the first and second arms
      define a nominal plane of the apparatus, and
      extend from the hub at an adjustable angle relative to each other
   first, second, and third legs, where
      the first leg extends from the hub and perpendicular to the nominal plane,
      the second leg extends from the first arm perpendicular to the nominal plane,
      the third leg extends from the second arm perpendicular to the nominal plane,
      a distance between the first and second legs is adjustable,
      a distance between the first and third legs is adjustable, and
      the first, second, and third legs have tips, and the tips of the first, second, and third legs define a pelvic plane having a predefined geometric relationship to the nominal plane of the apparatus.

2. The apparatus of claim 1 wherein the tip of at least one of the first, second, and third legs is pointed.

3. The apparatus of claim 1 where at least one of the first, second, or third legs is removable.

4. The apparatus of claim 1 where the pelvic plane is an ipsilateral hemipelvic plane of a patient that is substantially parallel to the nominal plane.

5. The apparatus of claim 1 where the distance between the first and third legs is set to a defined proportion of the distance between the first and second legs.

6. An apparatus for orienting a surgical instrument by establishing an ipsilateral hemipelvic reference plane at a hip of a subject, the apparatus comprising:
   a frame, the frame including a hub and first and second arms extending from said hub; and
   first, second, and third legs mounted to said frame, said first, second, and third legs terminating in tips, wherein said first leg is positioned at said hub, said second leg is positioned at said first arm, and said third leg is positioned at said second arm, wherein
      at least one of said first, second, and third legs is configured to contact an ilium portion of the subject's pelvis at a point having no palpable landmarks, and
      the apparatus defines the ipsilateral hemipelvic reference plane relative to the subject.

7. The apparatus of claim 6 wherein lengths of said first and second arms are adjustable relative to said hub.

8. The apparatus of claim 6 further comprising a guide that is adjustable with respect to the ipsilateral hemipelvic reference plane.

9. The apparatus of claim 6 wherein a distance between the tips of a first pair of said first, second, and third legs is adjustable to be a proportion of a distance between the tips of a second pair of said first, second, and third legs.

10. The apparatus of claim 9 wherein the proportion is between 70% and 100%.

11. An apparatus comprising:
    a hub;
    a first arm attached to and extending from the hub;
    a second arm attached to and extending from the hub, where the first and second arms extend from the hub at an angle relative to each other;
    first, second, and third legs, where
       the first leg extends from the hub and extends substantially perpendicular to the apparatus defined by the hub, first arm, and second arm,
       the second leg extends from the first arm and extends substantially perpendicular to the apparatus defined by the hub, first arm, and second arm,
       the third leg extends from the second arm and extends substantially perpendicular to the apparatus defined by the hub, the first arm, and the second arm,
       a distance between the first and second legs along a first length of the first arm is adjustable along the first length of the first arm,
       a distance between the first and third legs along a second length of the second arm is adjustable along the second length of the second arm, and the first, second, and third legs have tips, and the tips of the first, second, and third legs define a pelvic plane when the apparatus contacts a pelvis of a patient.

12. The apparatus of claim 11 where the angle between the first arm and the second arm is adjustable.

13. The apparatus of claim 11 wherein the tip of at least one of the first, second, and third legs is pointed.

14. The apparatus of claim 11 where at least one of the first, second, or third legs is removable.

15. The apparatus of claim 11 where the pelvic plane is an ipsilateral hemipelvic plane of a patient that is substantially parallel to the nominal plane.

16. The apparatus of claim 11 where the distance between the first and third legs is set to a defined proportion of the distance between the first and second legs.

17. The apparatus of claim 11 where one or more lengths of the first, second, and third legs are different.

18. The apparatus of claim 11 where lengths of the first, second, and third legs are substantially the same.

* * * * *

UNITED STATES PATENT AND TRADEMARK OFFICE
CERTIFICATE OF CORRECTION

PATENT NO.         : 11,490,832 B2
APPLICATION NO.    : 16/556844
DATED              : November 8, 2022
INVENTOR(S)        : Stephen B. Murphy Page 1 of 1

It is certified that error appears in the above-identified patent and that said Letters Patent is hereby corrected as shown below:

In the Claims

Column 11, Line 60, Claim 1 reads:
"the first leg extends from the hub and perpendicular to"
Should read:
"the first leg extends from the hub perpendicular to"

Signed and Sealed this
Twenty-third Day of July, 2024

Katherine Kelly Vidal
*Director of the United States Patent and Trademark Office*